(12) United States Patent
Kobayashi et al.

(10) Patent No.: US 10,022,139 B2
(45) Date of Patent: Jul. 17, 2018

(54) COLLECTION METHOD

(71) Applicant: TERUMO KABUSHIKI KAISHA, Shibuya-ku, Tokyo (JP)

(72) Inventors: Junichi Kobayashi, Fujinomiya (JP); Tomonori Hatta, Hadano (JP); Taiga Nakano, Isehara (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 317 days.

(21) Appl. No.: 14/795,755

(22) Filed: Jul. 9, 2015

(65) Prior Publication Data
US 2016/0113662 A1 Apr. 28, 2016

Related U.S. Application Data

(60) Provisional application No. 62/104,350, filed on Jan. 16, 2015.

(30) Foreign Application Priority Data

Oct. 27, 2014 (JP) .................................. 2014-218708

(51) Int. Cl.
*A61M 29/00* (2006.01)
*A61B 17/221* (2006.01)
(Continued)

(52) U.S. Cl.
CPC ............ *A61B 17/221* (2013.01); *A61F 2/013* (2013.01); *A61B 17/320758* (2013.01);
(Continued)

(58) Field of Classification Search
CPC .......... A61B 17/221; A61B 17/320758; A61B 2017/22002; A61B 2017/2212;
(Continued)

(56) References Cited

U.S. PATENT DOCUMENTS

| 6,740,061 B1 | 5/2004 | Oslund et al. |
| 2002/0111648 A1* | 8/2002 | Kusleika ................... A61F 2/01 606/200 |

(Continued)

FOREIGN PATENT DOCUMENTS

JP 2002-102231 A 4/2002

*Primary Examiner* — Tuan V Nguyen
(74) *Attorney, Agent, or Firm* — Buchanan Ingersoll & Rooney PC

(57) ABSTRACT

A medical device and collection method are disclosed which can effectively aspirate and remove substances collected inside a filter, and prevent the collected substances from dropping down from a filter portion. The collection method includes inserting a medical device having a filter portion in a contracted state into the living body lumen, installing the filter portion in the living body lumen by bringing the filter portion into the expanded state; collecting the substances inside the living body lumen using the filter portion; inserting an aspiration catheter which applies an aspiration force to a distal opening via a lumen formed inside the aspiration catheter, into the living body lumen along the shaft portion, and fitting the distal opening into the concave portion of the filter portion; aspirating the substances collected inside the concave portion using the aspiration catheter; and removing the filter portion from the inside of the living body lumen.

10 Claims, 13 Drawing Sheets

(51) Int. Cl.
*A61F 2/01* (2006.01)
*A61B 17/22* (2006.01)
*A61B 17/3207* (2006.01)
*A61B 17/32* (2006.01)

(52) U.S. Cl.
CPC ............ *A61B 2017/22002* (2013.01); *A61B 2017/2212* (2013.01); *A61B 2017/320004* (2013.01); *A61F 2002/016* (2013.01)

(58) Field of Classification Search
CPC ......... A61B 2017/320004; A61F 2/013; A61F 2002/016
See application file for complete search history.

(56) References Cited

U.S. PATENT DOCUMENTS

| | | | | |
|---|---|---|---|---|
| 2002/0173819 A1* | 11/2002 | Leeflang | ................ | A61B 17/22 606/200 |
| 2004/0006364 A1* | 1/2004 | Ladd | ................... | A61B 17/221 606/200 |
| 2013/0053882 A1* | 2/2013 | Hocking | ............. | A61B 17/221 606/200 |

\* cited by examiner

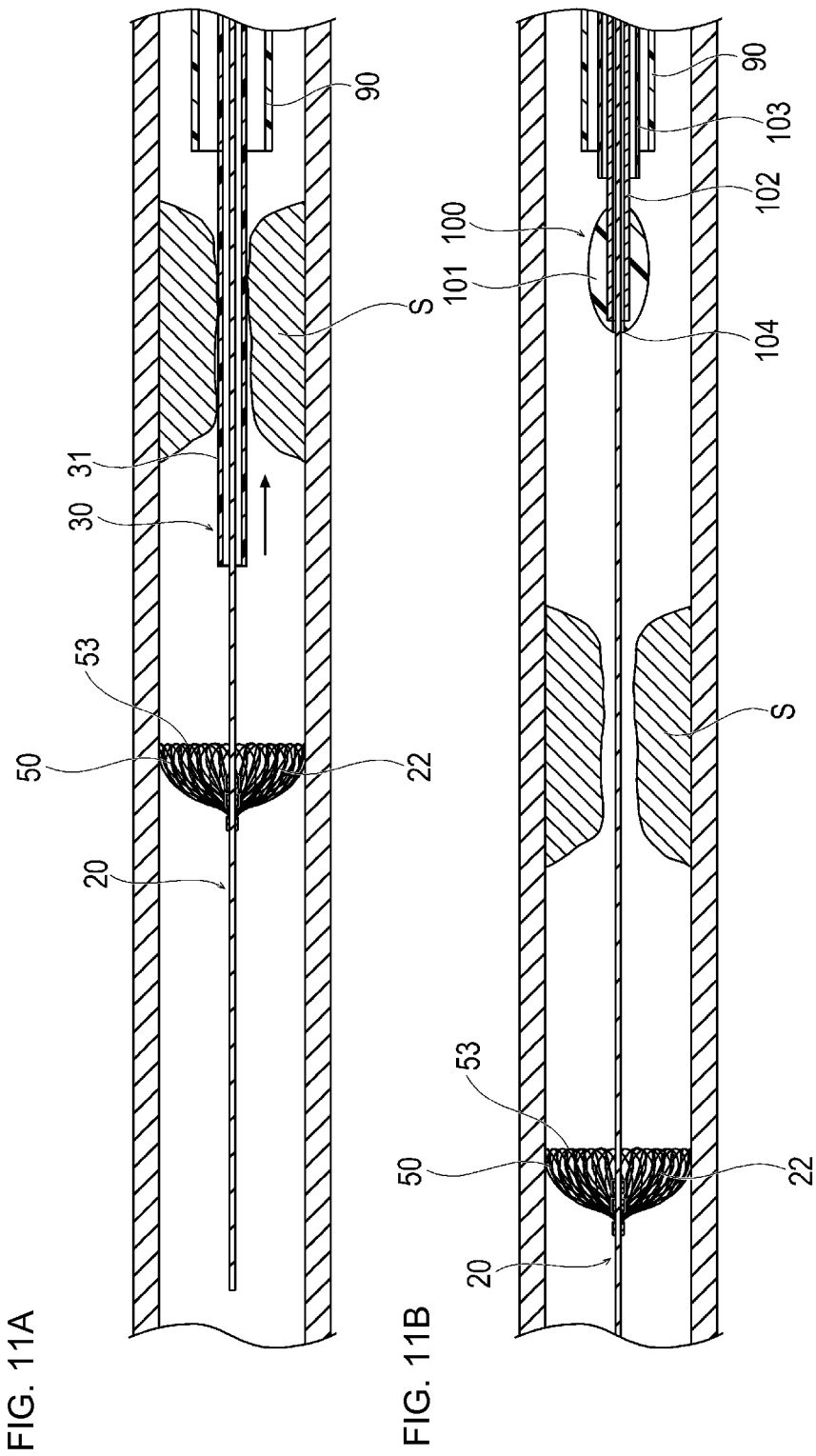

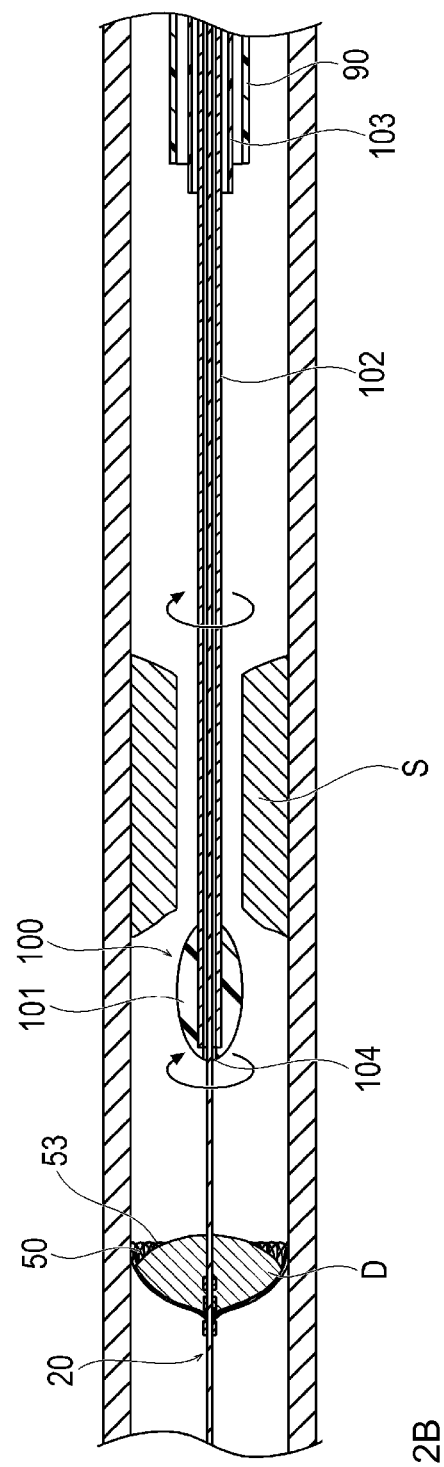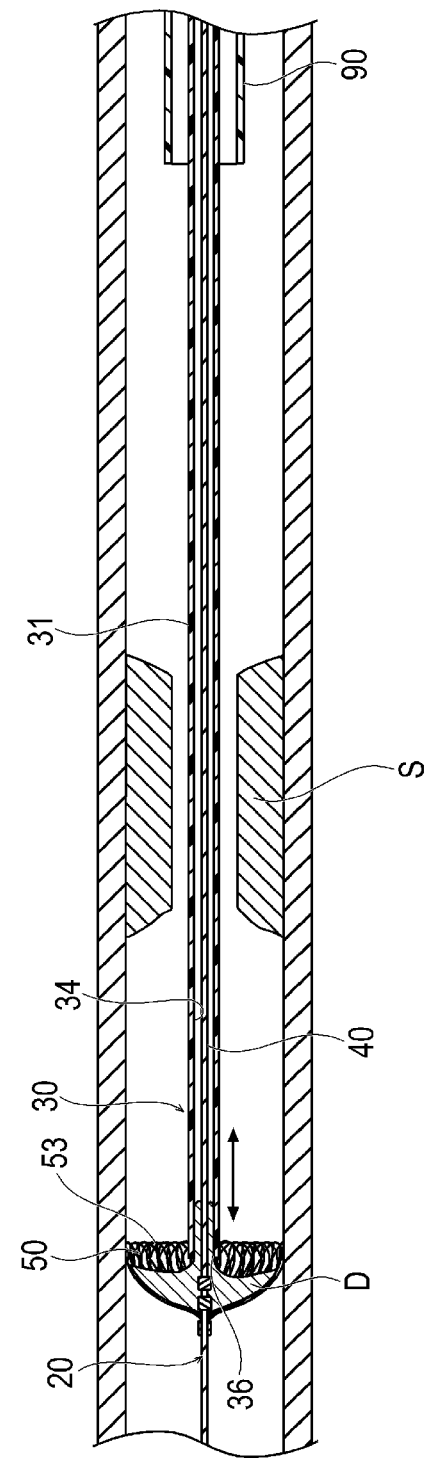

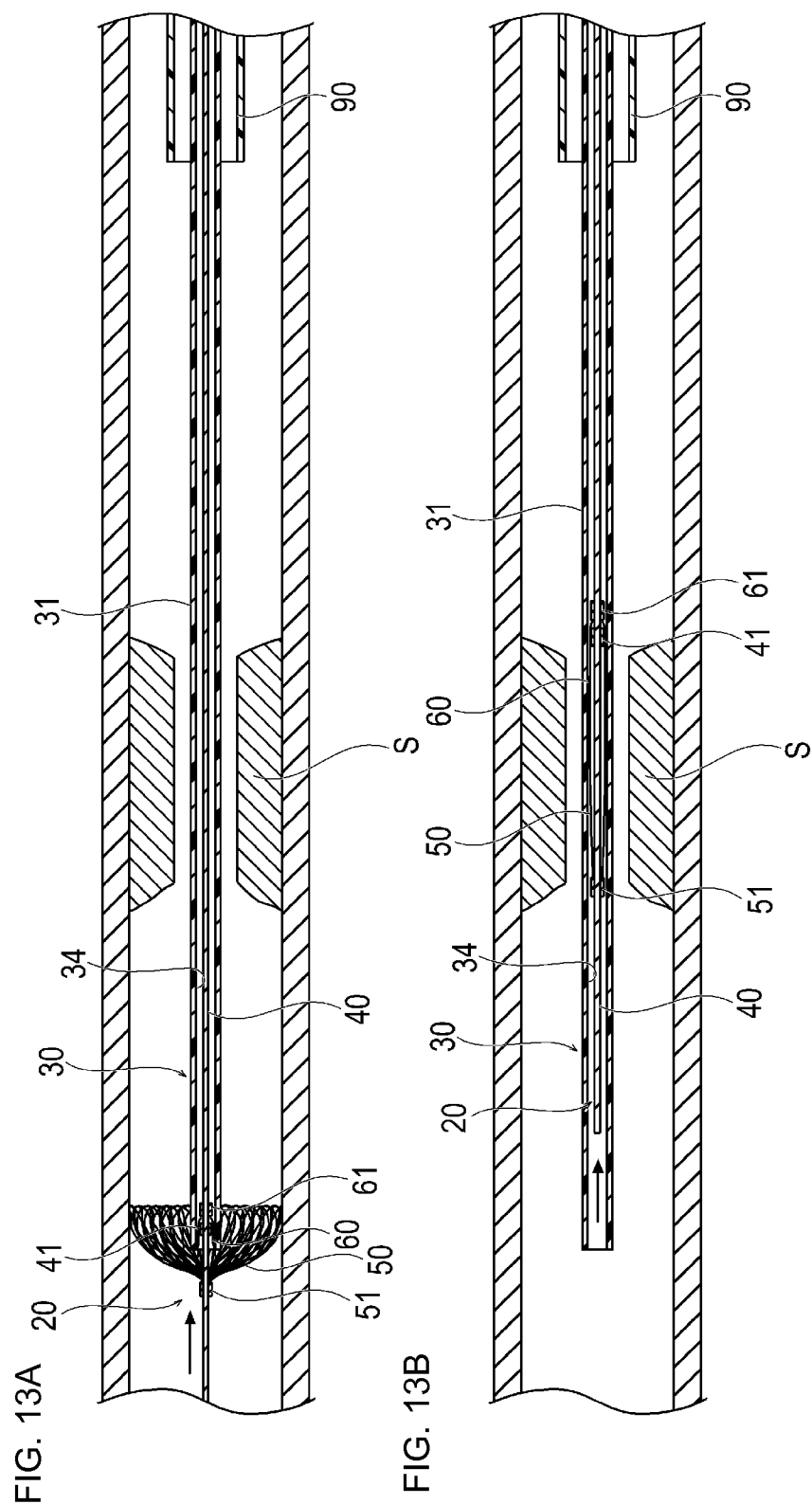

COLLECTION METHOD

CROSS-REFERENCES TO RELATED APPLICATIONS

This application claims priority to Japanese Application No. 2014-218708 filed on Oct. 27, 2014, and U.S. Provisional Application No. 62/104,350 filed on Jan. 16, 2015, which are incorporated herein by reference in their entirety.

TECHNICAL FIELD

The present disclosure generally relates to a medical device functioning as a filter inside a living body lumen and a collecting method for collecting substances inside the living body lumen by using the medical device.

BACKGROUND DISCUSSION

A method for treating stenosis caused by arterial plaque, a thrombus, or the like can include percutaneous transluminal coronary angioplasty (PTCA) for dilating a blood vessel by using a balloon, a method for causing a stent having a mesh shape or a coil shape to indwell into the blood vessel as a support for the blood vessel, and atherectomy for scraping off stenosis substances. Any one of these methods has a possibility that an object (debris) formed by stenosis substances being collapsed during treatment may flow through the blood vessel. If the debris flows to a peripheral blood vessel, there is a possibility that new stenosis may occur in the peripheral blood vessel. A method for preventing this possibility can include a method for collecting the debris by installing a wire-woven filter, which can expand and contract inside the blood vessel during treatment of a stenosed site and by using the filter, for example, refer to JP-A-2002-102231. However, in a case of treatment of the stenosed site in a thick and large blood vessel, a long stenosed site formed in arteries of the neck or lower limbs, the amount of debris can increase, thereby causing a possibility that the filter may eventually become full of debris. In this case, the debris cannot be collected by contracting the filter and pulling the filter into a guiding sheath. Thus, it can become necessary to withdraw the filter together with the guiding sheath from a living body while the filter remains in a state of protruding from the guiding sheath. Consequently, this case can require complicated manipulation skill, and the debris collected by the filter may be scattered to a peripheral portion.

As a countermeasure to be taken when a filter is full of debris, a method may be considered which decreases the amount of debris by causing a catheter to aspirate the debris inside the filter. Incidentally, a filter disclosed in JP-A-2002-102231 can be configured so that an edge portion of an opening for receiving the debris of the filter spreading in a basket shape is fixed to a shaft portion extending extracorporeally. Therefore, if an aspiration catheter is pushed into the filter by the above-described shaft portion serving as a guide, the aspiration catheter can be guided to an edge portion of the filter. However, the aspiration catheter cannot be guided into the filter where the debris is collected. Therefore, the debris collected in the filter cannot be effectively aspirated by using the aspiration catheter.

SUMMARY

In accordance with an exemplary embodiment, a medical device and a collecting method are disclosed, which can effectively aspirate and remove substances collected inside a filter, and which can help prevent the collected substances from dropping down from a filter portion.

In a medical device according to the present disclosure, which can achieve the above-described object, a medical device is disclosed for collecting substances inside a living body lumen, which can include an elongated shaft portion, a filter portion that has multiple gaps, that is formed in a net shape, and that is deformable to be in an expanded state where the filter portion has a basket shape so as to form a concave portion and is deformable from the expanded state to be in a contracted state where an opening end portion of the concave portion is contracted, and a support portion that is formed to include a gap larger than the gaps of the filter portion, and that can include an interlock portion interlocked with the opening end portion of the filter portion and a support side connection portion connected to the shaft portion. In the expanded state, the support side connection portion can be located inside the concave portion of the filter portion, and in the contracted state, the interlock portion contracts with the opening end portion, and the support side connection portion is located away from the filter portion so as to protrude outward from the concave portion.

In addition, a collecting method is disclosed according to the present disclosure, which can achieve the above-described object using the medical device, and can include (i) a step of inserting the filter portion in the contracted state into the living body lumen, (ii) a step of installing the filter portion in the living body lumen by bringing the filter portion into the expanded state, (iii) a step of collecting the substances inside the living body lumen by using the filter portion, (iv) a step of inserting an aspiration catheter which can apply aspiration force to a distal opening via a lumen formed inside the aspiration catheter, into the living body lumen along the shaft portion, and fitting the distal opening into the concave portion of the filter portion, (v) a step of aspirating the substances collected inside the concave portion by using the aspiration catheter, (vi) a step of bringing the filter portion into the contracted state, and (vii) a step of removing the filter portion from the inside of the living body lumen.

The medical device configured as described above can help enable an aspiration catheter to reach the inside of a concave portion by a shaft portion serving as a guide, which can be located inside the concave portion in an expanded state, and can effectively aspirate and remove substances contained inside the concave portion. Furthermore, when a filter portion collecting the substances is brought into a contracted state, since a gap of a support portion is larger than a gap of the filter portion, the substances can be held inside the filter portion after passing through the gap of the support portion. Accordingly, the collected substances can be prevented from dropping down from the filter portion.

In accordance with an exemplary embodiment, a configuration can be adopted in which the filter portion and the support portion are shaped so as to be in the expanded state in a state where an external force is not applied, the filter portion and the support portion can be brought into the expanded state by only releasing the restriction of the shape after being delivered into the living body lumen in the contracted state, thereby improving operability.

In accordance with an exemplary embodiment, a configuration can be adopted in which the support side connection portion has a through-hole formed therein, and the shaft portion is connected to the through-hole by slidably penetrating the through-hole, the shaft portion can be operated without moving the filter portion installed inside the living body lumen.

In accordance with an exemplary embodiment, a configuration can be adopted in which a filter side connection portion which has a through-hole formed therein and in which the shaft portion is connected to the through-hole by slidably penetrating the through-hole is disposed on a side opposite to the interlock portion of the filter in the contracted state, and in which the shaft portion has a stopper portion which is located between the support side connection portion and the filter side connection portion, and which has a size which is unable to pass through the support side connection portion and the filter side connection portion, the shaft portion can be moved independently from the filter portion within a predetermined range. In addition, the shaft portion can be operated without moving the filter portion. Furthermore, deformation or movement of the filter portion can be operated via the shaft portion by moving the shaft portion in an axial direction and bringing the stopper portion into contact with the support side connection portion or the filter side connection portion.

In accordance with an exemplary embodiment, a configuration can be adopted to further include a tubular sheath that can accommodate the filter portion and the support portion in the contracted state, and that can prevent the filter portion and the support portion from being deformed to be in the expanded state, the filter portion and the support portion which are in the contracted state can be delivered to a desired position by being accommodated inside the sheath. Accordingly, the filter portion and the support portion can be installed in the living body lumen after the filter portion and the support portion are brought into the expanded state by being released from the sheath.

In accordance with an exemplary embodiment, a configuration can be adopted in which at least a portion of the filter portion, the support portion, and the shaft portion includes an X-ray contrast property, a position can be accurately recognized by using X-ray contrast. Accordingly, the required manipulation skill becomes relatively easier.

In accordance with an exemplary embodiment according to the collecting method configured as described above, the distal opening portion of the aspiration catheter can be fitted into the concave portion of the filter portion by inserting the aspiration catheter into the living body lumen along the shaft portion. Therefore, the substances collected inside the concave portion can be effectively aspirated and removed using the aspiration catheter.

In accordance with an exemplary embodiment, a configuration can be adopted in which the collecting method further includes a step of scraping off stenosis substances or occluding substances formed inside the living body lumen on an upstream side of the filter portion, after the step of installing the filter portion in the living body lumen, and before the step of collecting the substances inside the living body lumen by using the filter portion, the substances generated by being scraped off are filtered and collected through the filter portion. In this manner, the collected substances can be effectively aspirated by using the aspiration catheter and the collected substances can be removed from the filter portion.

In accordance with an exemplary embodiment, a configuration of the collection method is adopted in which in the step of bringing the filter portion into the contracted state, the filter portion is brought into the contracted state by accommodating the filter portion inside the aspiration catheter, the filter portion can be contracted by utilizing the aspiration catheter, thereby improving workability.

A collecting method is disclosed for collecting substances inside a living body lumen using a medical device including an elongated shaft portion, a filter portion that has multiple gaps, that is formed in a net shape, and that is deformable to be in an expanded state where the filter portion has a basket shape so as to form a concave portion and is deformable from the expanded state to be in a contracted state where an opening end portion of the concave portion is contracted, and a support portion that is formed to include a gap larger than the gaps of the filter portion, and that includes an interlock portion interlocked with the opening end portion of the filter portion and a support side connection portion connected to the shaft portion, in which in the expanded state, the support side connection portion can be located inside the concave portion of the filter portion, and in the contracted state, the interlock portion contracts with the opening end portion, and the support side connection portion is located away from the filter portion so as to protrude outward from the concave portion, the method comprising: inserting the filter portion in the contracted state into the living body lumen; installing the filter portion in the living body lumen by bringing the filter portion into the expanded state; collecting the substances inside the living body lumen using the filter portion; inserting an aspiration catheter which applies an aspiration force to a distal opening via a lumen formed inside the aspiration catheter, into the living body lumen along the shaft portion, and fitting the distal opening into the concave portion of the filter portion; aspirating the substances collected inside the concave portion using the aspiration catheter; bringing the filter portion into the contracted state; and removing the filter portion from the inside of the living body lumen.

A collecting method is disclosed for collecting substances inside a living body lumen using a medical device, the medical device including an elongated shaft portion, a filter portion that is deformable in an expanded state, and wherein the filter portion has a basket shape so as to form a concave portion and is deformable from the expanded state to a contracted state where an opening end portion of the concave portion is contracted, and a support portion that includes an interlock portion interlocked with the opening end portion of the filter portion and a support side connection portion connected to the shaft portion, in which in the expanded state, the support side connection portion can be located inside the concave portion of the filter portion, and in the contracted state, the interlock portion contracts with the opening end portion, and the support side connection portion is located away from the filter portion so as to protrude outward from the concave portion, the method comprising: inserting the filter portion in the contracted state into the living body lumen; installing the filter portion in the living body lumen by bringing the filter portion into the expanded state; scraping off stenosis substances or occluding substances formed inside the living body lumen on an upstream side of the filter portion; collecting the substances inside the living body lumen using the filter portion; inserting an aspiration catheter which applies an aspiration force to a distal opening via a lumen formed inside the aspiration catheter, into the living body lumen along the shaft portion, and fitting the distal opening into the concave portion of the filter portion; aspirating the substances collected inside the concave portion using the aspiration catheter; bringing the filter portion into the contracted state; and removing the filter portion from the inside of the living body lumen.

BRIEF DESCRIPTION OF THE DRAWINGS

FIG. 11A is a schematic cross-sectional view illustrating a state inside the blood vessel when manipulation skill is used, for example, when a filter portion is expanded.

FIG. 11B is a schematic cross-sectional view illustrating a state when an atherectomy device is inserted into the blood vessel.

FIG. 12A is a schematic cross-sectional view illustrating a state inside the blood vessel when manipulation skill is used, for example, when occluding substances are scraped off by using the atherectomy device.

FIG. 12B is a schematic cross-sectional view illustrating a state when debris collected in the filter portion is aspirated by a catheter.

FIG. 13A is a schematic cross-sectional view illustrating a state inside the blood vessel when manipulation skill is used, for example, when the deformation portion is accommodated inside a pipe body.

FIG. 13B is a schematic cross-sectional view illustrating a state when the deformation portion is completely accommodated inside the pipe body.

DETAILED DESCRIPTION

Figure 1:
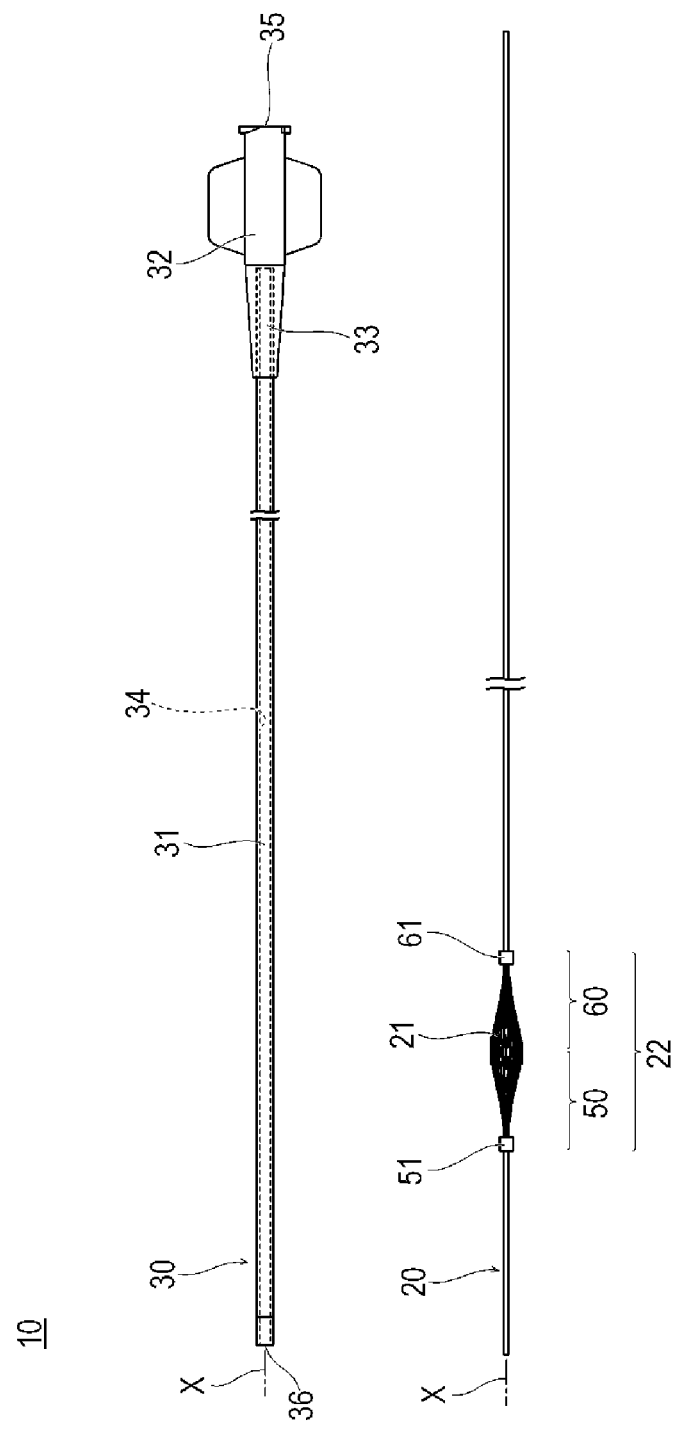
FIG. 1 is a plan view illustrating a medical device according to an exemplary embodiment.

Hereinafter, an embodiment according to the present disclosure will be described with reference to the drawings. In some cases, a dimension ratio in the drawings may be exaggerated and different from a ratio used in practice in order to facilitate the description.

A medical device 10 according to the embodiment of the present disclosure can be used in treating (taking measures for) a stenosed site or an occluded site caused by plaque, a thrombus, or the like inside a blood vessel. In accordance with an exemplary embodiment, the medical device can be used in order to collect debris (substances) which are dropping down from the stenosed site or the occluded site and flowing inside the blood vessel. In the description, a side of the device which is inserted into the blood vessel is referred to as a "distal side", and an operating hand side is referred to as a "proximal side". In addition, the debris is not necessarily limited to the substances dropping down from the stenosed site or the occluded site, and all substances which can be present inside a living body lumen can be referred to as the debris.

Figure 2:
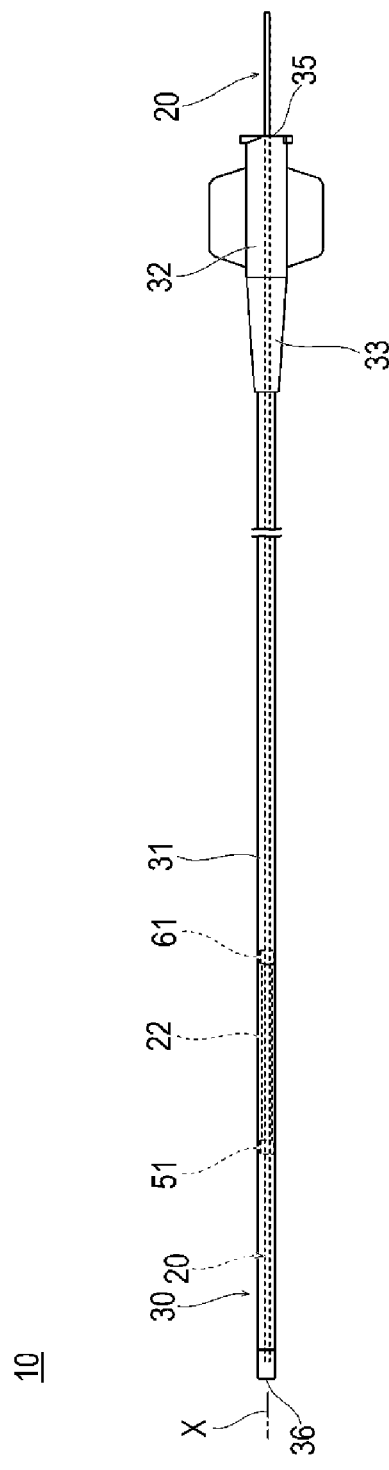
FIG. 2 is a plan view illustrating a state where a filter device of the medical device according to the exemplary embodiment is accommodated inside a sheath.

As illustrated in FIGS. 1 and 2, the medical device 10 according to the embodiment of the present disclosure can include a filter device 20 including a function as a filter, and a sheath 30 which can accommodate the filter device 20.

The filter device 20 can include a deformation portion 22 which is deformable and can include multiple interwoven wires 21, and an elongated shaft portion 40 which can penetrate the deformation portion 22.

Figure 3:
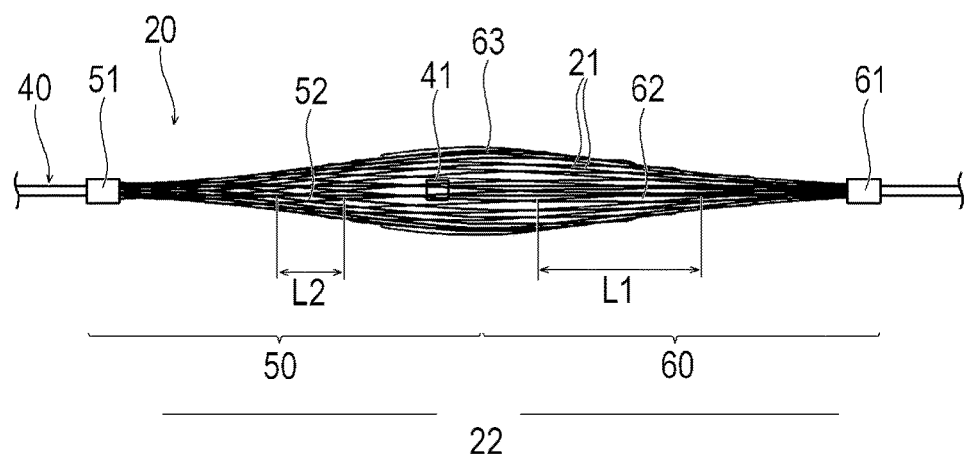
FIG. 3 is a plan view illustrating a deformation portion in a contracted state of the medical device according to the exemplary embodiment.
Figure 4:
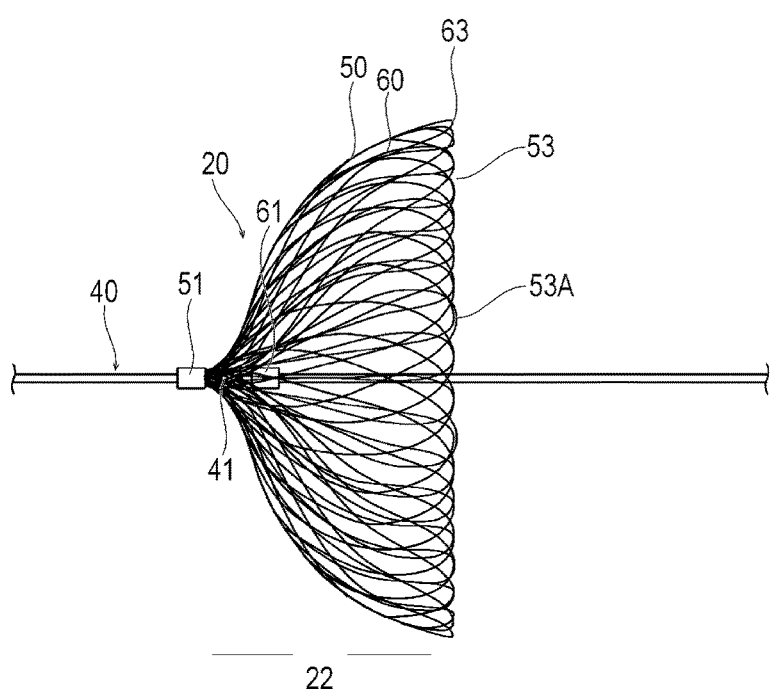
FIG. 4 is a plan view illustrating the deformation portion in an expanded state of the medical device according to the exemplary embodiment.

As illustrated in FIGS. 3 and 4, the deformation portion 22 can include a filter portion 50 which functions as a filter, and a support portion 60 which supports the filter portions 50 by being located on the proximal side of the filter portion 50. The support portion 60 can be interlocked with the filter portion 50 by an interlock portion 63, thereby supporting the support portion 60. A filter side connection portion 51 to which the shaft portion 40 can be connected is disposed on the distal side of the filter portion 50, and a support side connection portion 61 to which the shaft portion 40 can be connected is disposed on the proximal side of the support portion 60. The filter portion 50 can be formed in a tubular shape (annular shape) so as to have gaps 52 between wires 21 by interweaving the multiple wires 21. In addition, the support portion 60 can also be formed in a tubular shape (annular shape) so as to have gaps 62 between wires 21 by interweaving the multiple wires 21. The filter portion 50 and the support portion 60 can be continuously formed by using the same wires 21. A pitch (advanced distance in the axial direction X while a spiral winds one round) of the respective wires 21 in the support portion 60 is longer than a pitch of the respective wires 21 in the filter portion 50. Therefore, an axial length L1 of the respective gaps 62 formed in the support portion 60 is longer than an axial length L2 of the respective gaps 52 formed in the filter portion 50. Accordingly, an area of the respective gaps 62 formed in the support portion 60 is larger than an area of the respective gaps 52 formed in the filter portion 50.

As illustrated in FIG. 3, the deformation portion 22 is deformable to be in a contracted state where an outer diameter of the deformation portion 22 is contracted by the filter side connection portion 51 and the support side connection portion 61 being separated from each other, and is deformable to be in an expanded state where the filter side connection portion 51 and the support side connection portion 61 are moved close to each other and deformed in a basket shape.

As illustrated in FIG. 4, the filter portion 50 in the expanded state has the basket shape so as to form a concave portion 53 which opens toward the support portion 60 side, that is, toward the proximal side. At this time, the support portion 60 is folded back to an inner side of the concave portion 53 from an opening end portion 53A of the concave portion 53, and is arranged inside the concave portion 53 in the basket shape so as not to overlap the filter portion 50.

The number of wires 21 is not particularly limited, and can be 72, for example. A condition for interweaving the wires 21 is not particularly limited, and the wires 21 are interwoven by using, for example, a two-under and two-over pattern.

The outer diameter of the wires 21 can be appropriately selected depending on a material of the wires 21 or use of the deformation portion 22, and can be, for example, 20 μm to 100 μm. As an example, the outer diameter can be set to 40 μm.

As a configuration material of the wires 21, a flexible material is preferably used. For example, a shape memory alloy can be used for which a shape memory effect and superelasticity can be provided by heat treatment, stainless steel, Ta, Ti, Pt, Au, W, polyolefin such as polyethylene, or polypropylene, polyester such as polyamide, or polyethylene terephthalate, fluorinated polymer such as ETFE, polyether ether ketone (PEEK), or polyimide. As the shape memory alloy, a Ni—Ti based alloy, a Cu—Al—Ni based alloy, a Cu—Zn—Al based alloy, a combination thereof, or the like can be preferably used. For example, a structure having multiple materials combined therein can include a structure in which a core wire made of Pt is coated with the Ni—Ti alloy in order to provide contrast performance, or a structure in which a core wire made of the Ni—Ti alloy is subjected to gold plating.

Figure 5:
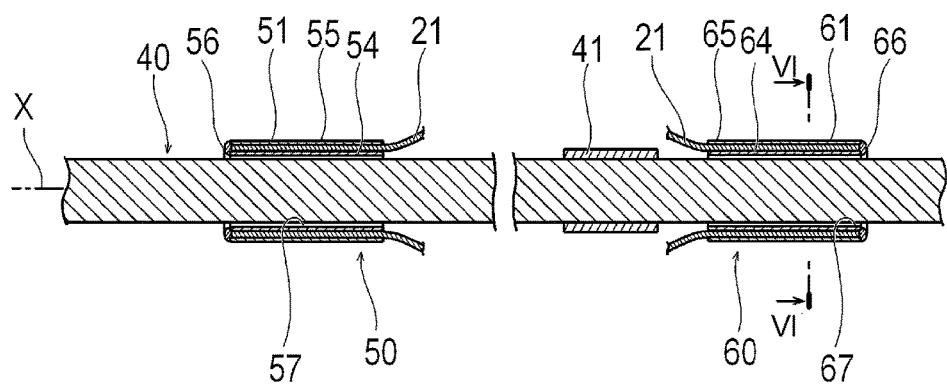
FIG. 5 is a cross-sectional view of a support side connection portion and a filter side connection portion.
Figure 6:
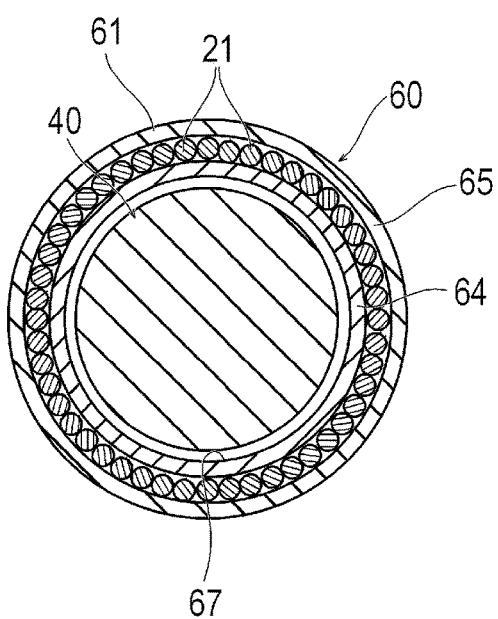
FIG. 6 is a cross-sectional view taken along line VI-VI in FIG. 5.

As illustrated in FIGS. 5 and 6, the support side connection portion 61 can include an inner tube 64 located inside the wire 21, an outer tube 65 located outside the wire 21, and a joining portion 66 for joining the inner tube 64 and the outer tube 65 at end portions of the inner tube 64 and the outer tube 65. The wire 21 can be fixedly interposed between the inner tube 64 and the outer tube 65. In accordance with an exemplary embodiment, it can be preferable to fill a portion between the inner tube 64 and the outer tube 65 with an adhesive. However, as long as the wire 21 can be fixed, the portion may not be filled with the adhesive. For example, the joining portion 66 is formed by means of silver brazing or soldering. As long as the wire 21 can be fixed, the joining portion 66 may not be disposed therein.

As illustrated in FIG. 5, the filter side connection portion 51 can include an inner tube 54 located inside the wire 21, an outer tube 55 located outside the wire 21, and a joining portion 56 for joining the inner tube 54 and the outer tube 55 at end portions of the inner tube 54 and the outer tube 55. The wire 21 can be fixedly interposed between the inner tube 54 and the outer tube 55. It can be preferable to fill a portion between the inner tube 54 and the outer tube 55 with an adhesive. However, as long as the wire 21 can be fixed, the portion between the inner tube 54 and the outer tube 55 may not be filled with the adhesive. For example, the joining portion 56 can be formed by means of silver brazing or soldering. As long as the wire 21 can be fixed, the joining portion 56 may not be disposed in between the inner tube 54 and the outer tube 55.

The outer diameter of the outer tubes 55 and 65 is not particularly limited. However, for example, the outer diameter may be 0.3 mm to 1.5 mm. As an example, 0.65 mm to 0.70 mm can be employed. The inner diameter of the inner tubes 54 and 64 is not particularly limited. However, for example, the inner diameter may be 0.1 mm to 1.0 mm. As an example, 0.25 mm to 0.30 mm can be employed.

A configuration material of the inner tubes 54 and 55 and the outer tubes 55 and 65 is not particularly limited. However, for example, stainless steel, a shape memory alloy, or the like can be preferably used.

As illustrated in FIG. 4, the deformation portion 22 is in an expanded state when remaining in a natural state where an external force is not applied thereto. As illustrated in FIG. 3, the deformation portion 22 can be brought into a contracted state by an external force being applied thereto so that the filter side connection portion 51 and the support side connection portion 61 are separated from each other. The outer diameter of the deformation portion 22 in the expanded state can be appropriately selected depending on the inner diameter of the blood vessel for application. However, for example, the outer diameter may be 1 mm to 15 mm. As an example, 7 mm can be employed. The outer diameter of the deformation portion 22 in a contracted state can be appropriately selected depending on the inner diameter of the blood vessel for application. However, for example, the outer diameter may be 0.3 mm to 1.5 mm. A length in an axial direction X of the deformation portion 22 in the contracted state can be appropriately selected depending on the inner diameter of the blood vessel for application. However, for example, the length may be 20 mm to 50 mm. As an example, 30 mm can be employed.

Figure 7:
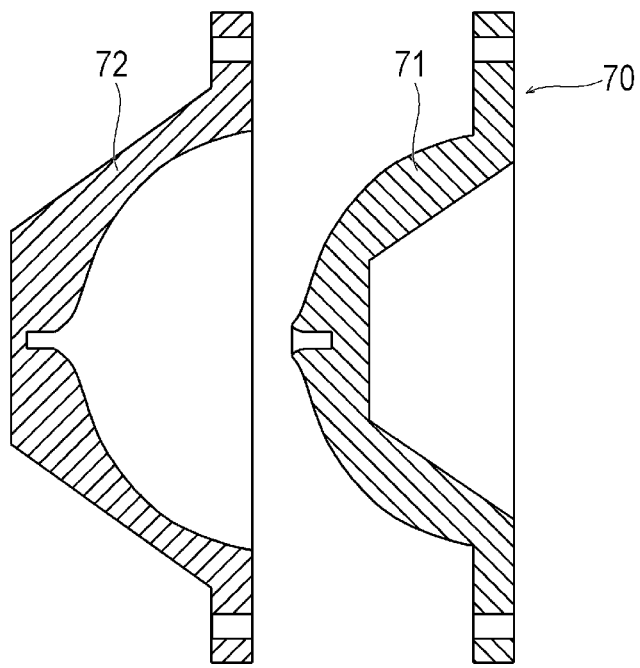
FIG. 7 is a cross-sectional view illustrating a molding die for performing shape memory processing on the deformation portion.
Figure 8:
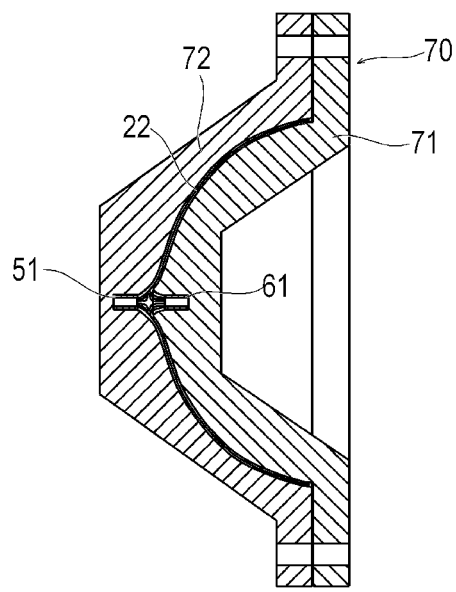
FIG. 8 is a cross-sectional view illustrating that the deformation portion is installed in the molding die in order to perform the shape memory processing on the deformation portion.

This deformation portion 22 can be formed by deforming the wire 21 so as to be in an expanded state and performing shape memory processing thereon after the wire 21 made of a shape memory alloy is interwoven in a tubular shape. As an example of a method for performing the shape memory processing, the interwoven wires 21 can be first fixed to the support side connection portion 61 and the filter side connection portion 51, and a mold 70 (refer to FIG. 7) which can maintain the deformation portion 22 so as to be in the expanded state is prepared. The mold 70 can include a first mold 71 and a second mold 72, which can interpose the deformation portion 22 between the first and second molds 71, 72. As illustrated in FIG. 8, the deformation portion 22 in the expanded state can be accommodated between the first mold 71 and the second mold 72, and the shape memory processing can be performed by heating the mold 70. In this manner, a shape of the deformation portion 22 is memorized in the expanded state. Heating temperature is appropriately set depending on the configuration material or the like of the wire 21. However, for example, in a case where the material is a Ni—Ti alloy, the temperature can be, for example, 600° to 700°. A heating time period is appropriately set depending on the configuration material or the like of the wire 21. However, for example, in a case where the material is a Ni—Ti alloy, the time period can be, for example, 3 minutes to 30 minutes.

As illustrated in FIG. 5, the shaft portion 40 penetrates a through-hole 57 of the filter side connection portion 51 and a through-hole 67 of the support side connection portion 61, and is slidable on the filter side connection portion 51 and the support side connection portion 61. A stopper portion 41 which is a tubular body having a size which cannot pass through the through-holes of the filter side connection portion 51 and the support side connection portion 61 is fixed to the shaft portion 40 at a position interposed between the filter side connection portion 51 and the support side connection portion 61. The stopper portion 41 is movable in the axial direction X between the filter side connection portion 51 and the support side connection portion 61, and is rotatable around the shaft portion 40 with respect to the filter side connection portion 51 and the support side connection portion 61.

A configuration material of the shaft portion 40 is not particularly limited. However, for example, stainless steel, a shape memory alloy, or the like can be used.

As illustrated in FIGS. 1 and 2, the sheath 30 can include a tubular body 31, a hub 32, and an anti-kink protector 33. The tubular body 31 can include a lumen 34 which can accommodate the filter device 20, and is open in a tubular body opening 36 formed on the distal end portion. The hub 32 is fixed to the proximal end portion of the tubular body 31, and can include a hub opening 35 which communicates with the lumen 34. The anti-kink protector 33 is a flexible member for covering a connection portion between the tubular body 31 and the hub 32, and suppresses kinking of the tubular body 31.

A configuration material of the tubular body 31 is not particularly limited. However, for example, polyolefin such as polyethylene, polypropylene, ethylene-propylene copolymer, or ethylene-vinyl acetate copolymer, polyvinyl chloride, polystyrene, polyamide, polyimide, or a combination thereof can be used. The tubular body 31 may be configured to include multiple materials, or may be configured so that a reinforcing member such as a wire or the like may be embedded therein.

Next, a method of using the medical device 10 according to the present embodiment will be described by using an example where the medical device 10 is applied to atherectomy.

Figure 9A:
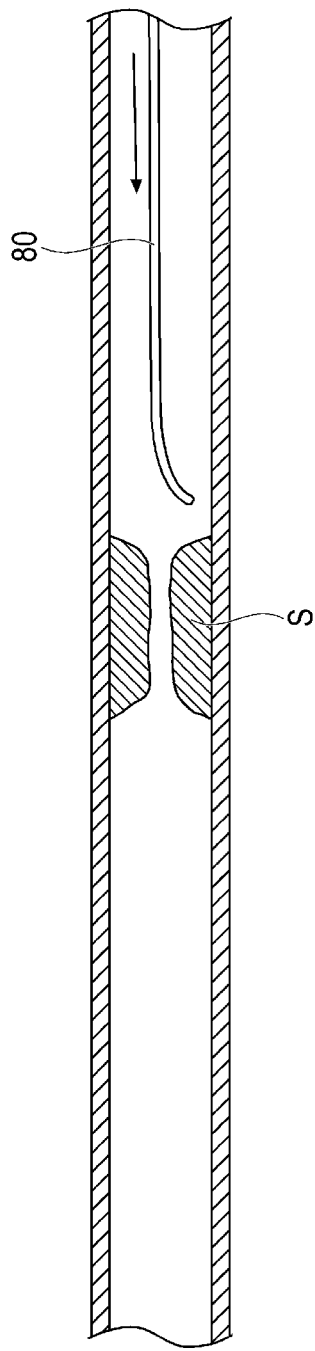
FIG. 9A is a schematic cross-sectional view illustrating a state inside a blood vessel when manipulation skill is used, for example, when a guidewire is inserted into the blood vessel.
Figure 9B:
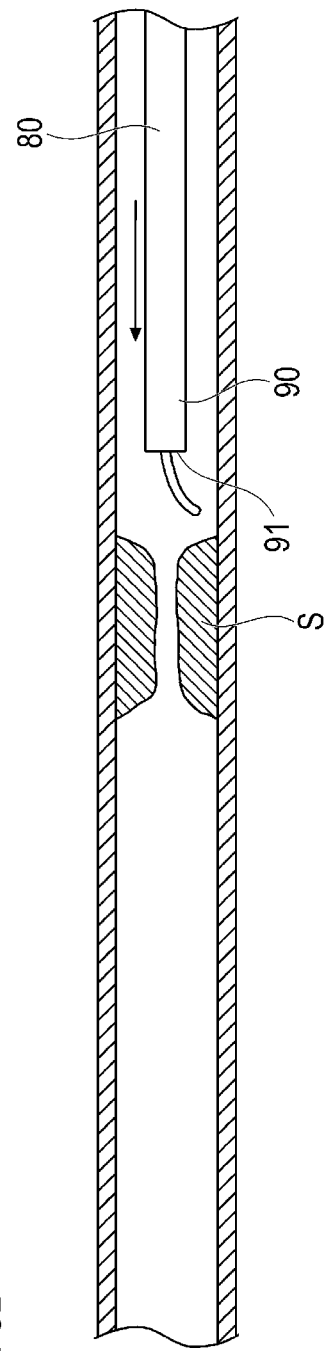
FIG. 9B is a schematic cross-sectional view illustrating a state when a guiding catheter is inserted into the blood vessel.

First, an introducer sheath (not illustrated) is percutaneously inserted into the blood vessel on an upstream side (proximal side) from a stenosed site S in the blood vessel, and a guidewire 80 is inserted into the blood vessel via the introducer sheath. Then, the guidewire 80 is pushed forward so as to reach the proximal side of the stenosed site S, as illustrated in FIG. 9A. Thereafter, the proximal end portion of the guide wire 80 located extracorporeally is inserted into a catheter opening 91 on a distal side of a guiding catheter 90. As illustrated in FIG. 9B, the guiding catheter 90 is inserted into the blood vessel along the guidewire 80 so as to reach the proximal side of the stenosed site S.

Figure 10A:
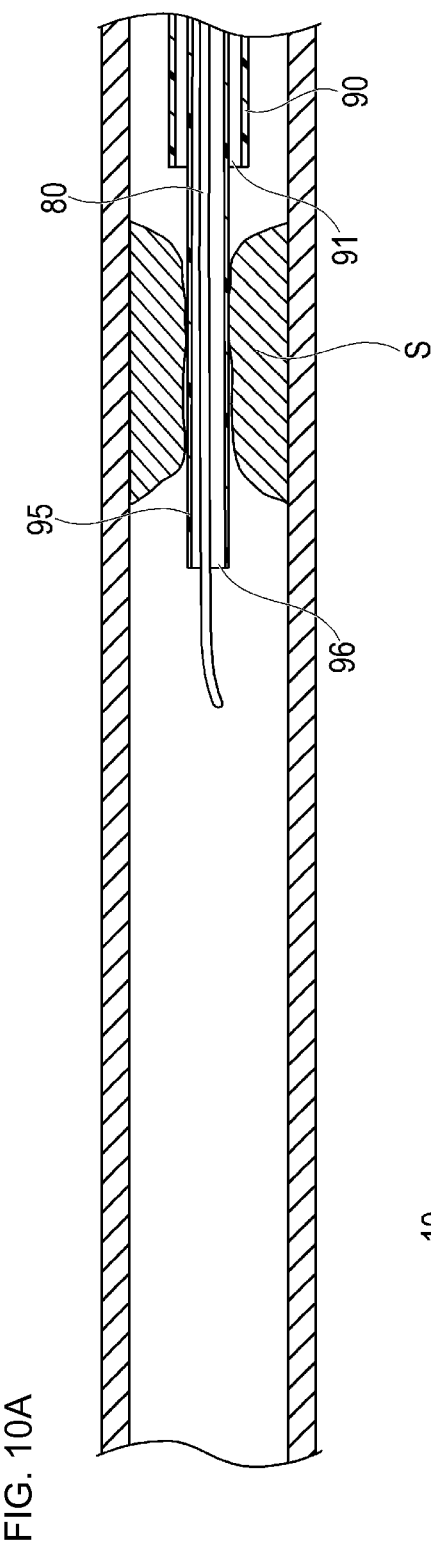
FIG. 10A is a schematic cross-sectional view illustrating a state inside the blood vessel when manipulation skill is used, for example, when the guidewire is removed from the blood vessel.

Next, the proximal end portion of the guidewire 80 located extracorporeally is inserted into a catheter opening 96 on the distal side of a support catheter 95, and the support catheter 95 is pushed forward to reach the proximal side of the stenosed site S. Thereafter, as illustrated in FIG. 10A, the support catheter 95 and the guidewire 80 are caused to reach the distal side from the stenosed site S. Thereafter, the guidewire 80 is removed in a state where the support catheter 95 remains inside the blood vessel.

Figure 10B:
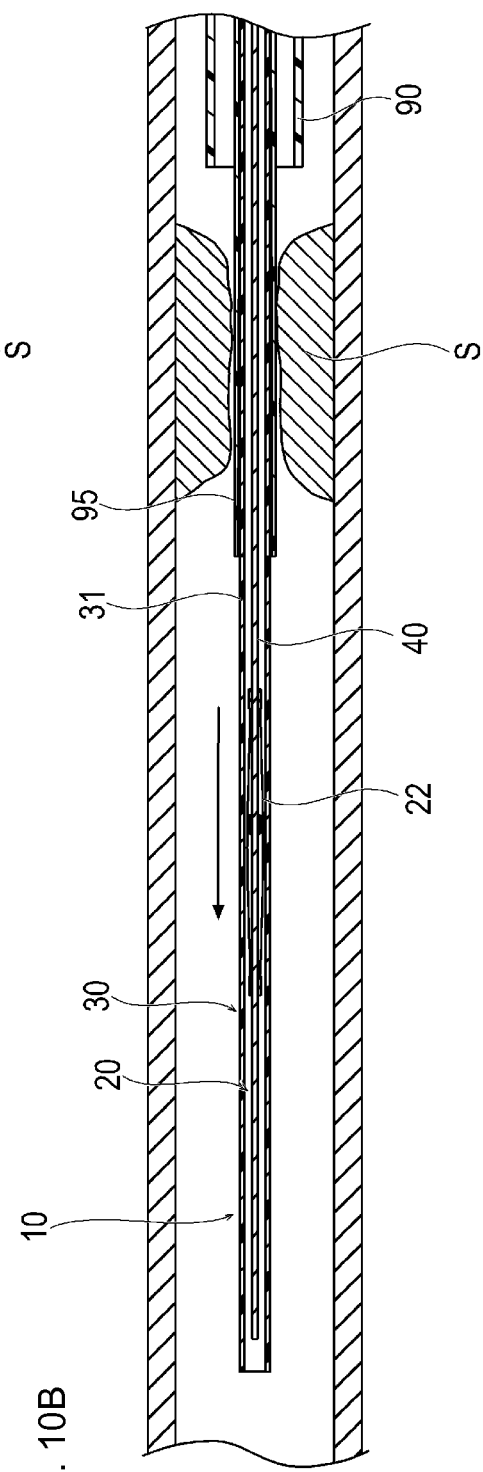
FIG. 10B is a schematic cross-sectional view illustrating a state when the medical device is inserted into the blood vessel.

Next, as illustrated in FIG. 2, the medical device 10 which accommodates the filter device 20 inside the sheath 30 is prepared. The deformation portion 22 is arranged at a position close to the distal end portion of the tubular body 31 of the sheath 30, and a shape of the deformation portion 22 is restricted in a contracted state. The shaft portion 40 protrudes to the proximal side from the hub opening 35 of the hub 32. Then, as illustrated in FIG. 10B, the medical device 10 is inserted into the blood vessel via the support catheter 95 so as to reach the distal side from the stenosed site S. Thereafter, the support catheter 95 is removed.

Then, the sheath 30 is moved relatively to the proximal side from the filter device 20, and the deformation portion 22 is caused to protrude to the distal side from the tubular body 31. In this manner, as illustrated in FIG. 11A, the deformation portion 22 is brought into an expanded state by its own restoring force. An outer peripheral portion of the filter portion 50, which has a basket shape comes into contact with an inner wall surface of the blood vessel. At this time, the concave portion 53 of the filter portion 50 is open toward the stenosed site S on the upstream side (proximal side). Thereafter, the sheath 30 is removed by leaving the filter device 20 behind.

Then, as illustrated in FIG. 11B, an atherectomy device 100 is inserted into the blood vessel via the guiding catheter 90. In brief, the atherectomy device 100 can include a rotary member 101 which is rotatably located on the distal side, a drive shaft 102 which is fixed to the proximal side of the rotary member 101 so as to rotate the rotary member 101, and an outer tube 103 having a tubular shape in which the drive shaft 102 is rotatably accommodated on the proximal side from the rotary member 101. A distal end opening 104 communicating with the drive shaft 102 is formed on the distal side of the rotary member 101. Many fine particles for scraping off occluding substances adhere to an outer surface on the distal side of the rotary member 101. The drive shaft 102 is configured so that the proximal end portion is connected to a gas turbine, and thus is rotatably driven by high pressure gas such as nitrogen gas or the like. A drive source is not limited to the gas turbine. For example, a motor or the like may be employed.

When the atherectomy device 100 is inserted into the blood vessel, the proximal end portion of the shaft portion 40 is inserted into the distal opening 104 so as to reach the inside of the blood vessel via the guiding catheter 90. Then, the rotary member 101 is arranged on the proximal side of the stenosed site S. If the rotary member 101 is rotatably driven and pushed forward to the distal side by the drive shaft 102, as illustrated in FIG. 12A, the particles on the outer surface of the rotary member 101 come into contact with stenosis substances of the stenosed site S. The stenosis substances are scraped off and flow to the distal side (downstream side) after becoming debris D. The debris D flowing to the distal side enters the inside of the concave portion 53 of the filter portion 50 located on the distal side, and is collected so as to be filtered by the filter portion 50, which can help prevent the debris D from flowing to a peripheral portion, and can help prevent a new stenosed site from occurring in the peripheral blood vessel. After the stenosis substances are completely scraped off, the drive shaft 102 is stopped, and the atherectomy device 100 is removed via the guiding catheter 90.

Then, the proximal end portion of the shaft portion 40 is inserted into the tubular body opening 36 of the sheath 30 (aspiration catheter). As illustrated in FIG. 12B, the sheath 30 is inserted into the blood vessel via the guiding catheter 90. If the sheath 30 is further pushed forward, the tubular body opening 36 of the sheath 30 is guided by the shaft portion 40 penetrating the substantially center portion of the concave portion 53 of the filter portion 50, and reaches the inside of the concave portion 53. In this state, a Y-connector (not illustrated) is connected so as to communicate with the hub opening 35 of the sheath 30, and a syringe is connected to an opening of the Y-connector on a side into which the shaft portion 40 is not inserted. Thereafter, if aspiration force is applied by drawing a plunger of the syringe, negative pressure can be generated inside the lumen 34 extending from the distal side to the proximal side. In this manner, the debris D inside the filter portion 50 can be drawn into the lumen 34 from the tubular body opening 36. When the debris D is aspirated by the syringe, the tubular body 31 is moved forward and rearward inside the filter portion 50, if necessary. In this manner, the debris D can be effectively aspirated. As described above, the debris D inside the filter portion 50 can be partially or completely aspirated, and can be drawn into the lumen 34, thereby bringing the filter portion 50 into a state where the filter portion 50 is likely to contract. A device for aspirating the debris D (aspiration catheter) may be a catheter different from the sheath 30. In addition, a device for applying the aspiration force is not limited to the syringe. For example, a pump may be employed.

Then, if the shaft portion 40 is moved relatively to the proximal side from the sheath 30, as illustrated in FIG. 13A, the stopper portion 41 fixed to the shaft portion 40 presses the support side connection portion 61 toward the proximal side so as to move into the lumen 34 of the tubular body 31 together with the support side connection portion 61. In this manner, as illustrated in FIG. 13B, the support portion 60 fixed to the support side connection portion 61 can be dragged into the lumen 34. Furthermore, the filter portion 50 connected to the support portion 60 can also be contracted and dragged into the lumen 34. At this time, the support portion 60, which is concave by overlapping the inner side of the concave portion 53 of the filter portion 50 is deformed so that an inner side surface of the support portion 60 is reversed to become a tubular shaped outer peripheral surface. However, even when the debris D remains inside the concave portion 53, since the gap 62 of the support portion 60 is larger than the gap 52 of the filter portion 50, the debris D can be less likely to be caught on the support portion 60 moving so as to be separated from the filter portion 50. Therefore, the debris D passes through the gap 62 of the support portion 60, and is accommodated inside the tubular body 31 together with the filter portion 50 while a state where the debris D is accommodated inside the concave portion 53 of the filter portion 50 is maintained. As described above, when the filter portion 50 is accommodated inside the tubular body 31, the debris D can be prevented from being caught on the support portion 60 and being separated from the filter portion 50. When the debris D is aspirated by using an aspiration catheter different from the sheath 30, instead of the sheath 30, the filter portion 50 may be removed by being accommodated inside the aspiration catheter.

Thereafter, the filter device 20 is removed together with the sheath 30, and the guiding catheter 90 and the introducer sheath are removed. In this manner, the manipulation skill is completed.

As described above, the medical device 10 according to the embodiment has the elongated shaft portion 40, the filter portion 50 which is formed in a net shape including the multiple gaps 52, and which is deformable between the expanded state in a basket shape so as to form the concave portion 53 and the contracted state in which the opening end portion 53A of the concave portion 53 is contracted from the expanded state, and the support portion 60 which is formed to include the gap 62 larger than the gap 52 of the filter portion 50, and which can include the interlock portion 63 interlocked with the opening end portion 53A of the filter portion 50 and the support side connection portion 61 connected to the shaft portion 40. In the expanded state, the support side connection portion 61 can be located inside the concave portion 53 of the filter portion 50. In the contracted state, the interlock portion 63 contracts with the opening end portion 53A, and the support side connection portion 61 is located by being separated from the filter portion 50 so as to protrude outward from the concave portion 53. Therefore, the medical device 10 can effectively aspirate the debris D collected inside the concave portion 53 in such a way that the filter portion 50 which is delivered into the living body lumen in the contracted state is expanded and installed inside the living body lumen, the filter portion 50 is caused to function as the filter, and the aspiration catheter is caused to reach the inside of the concave portion 53 by using the shaft portion 40 reaching the inside of the concave portion 53 as the guide. Furthermore, when the filter portion 50 collecting the debris D is brought into the contracted state, since the gap 62 of the support portion 60 is larger than the gap 52 of the filter portion 50, the debris D passes through the gap 62 of the support portion 60, and is held inside the filter portion 50. Accordingly, the debris D can be prevented from dropping down from the filter portion 50. Therefore, restenosis can be prevented from occurring in a peripheral portion.

In addition, the filter portion 50 and the support portion 60 are shaped so as to be in an expanded state, in a natural state where an external force is not applied. The filter portion 50 and the support portion 60 can be brought into the expanded state by only releasing restriction in the shape after being delivered into the living body lumen in a contracted state, thereby improving operability.

In addition, the support side connection portion 61 is connected to the shaft portion 40 in such a way that the through-hole 67 is formed therein, and the shaft portion 40 penetrates the through-hole 67 so as to be slidable. Therefore, without moving the filter portion 50 installed inside the living body lumen, it is possible to operate only the shaft portion 40.

In addition, the through-hole 57 is formed on the side opposite to the interlock portion 63 of the filter portion 50 in the contacted state, and the filter side connection portion 51 connected to the shaft portion 40 by the shaft portion 40 penetrating the through-hole 57 so as to be slidable is disposed therein. The shaft portion 40 is located between the support side connection portion 61 and the filter side connection portion 51, and has the stopper portion 41 having a size which cannot pass through the support side connection portion 61 and the filter side connection portion 51. Therefore, the shaft portion 40 can be moved independently from the filter portion 50 within a predetermined range. Without moving the filter portion 50, it is possible to operate only the shaft portion 40. Furthermore, the shaft portion 40 is moved, and the stopper portion 41 is brought into contact with the support side connection portion 61 or the filter side connection portion 51. In this manner, the deformation or the movement of the filter portion 50 can be operated via the shaft portion 40.

In addition, the medical device 10 has the tubular sheath 30 which accommodates the filter portion 50 and the support portion 60 in the contracted state, and which can help prevent the filter portion 50 and the support portion 60 from being deformed to be in the expanded state. Accordingly, the filter portion 50 and the support portion 60 which are in the contracted state can be delivered to a desired position by being accommodated inside the sheath 30. Therefore, the filter portion 50 and the support portion 60 can be installed into the living body lumen after the filter portion 50 and the support portion 60 are brought into the expanded state by being released from the sheath 30.

In addition, the present disclosure provides a method of collecting debris (substances) inside the living body lumen. The method is performed by using a medical device including an elongated shaft portion, a filter portion that has multiple gaps, that is formed in a net shape, and that is deformable to be in an expanded state where the filter portion has a basket shape so as to form a concave portion and is deformable from the expanded state to be in a contracted state where an opening end portion of the concave portion is contracted, and a support portion that is formed to include a gap larger than the gaps of the filter portion, and can include an interlock portion interlocked with the opening end portion of the filter portion and a support side connection portion connected to the shaft portion, in which in the expanded state, the support side connection portion can be located inside the concave portion of the filter portion, and in the contracted state, the interlock portion contracts with the opening end portion and the support side connection portion is located away from the filter portion so as to protrude outward from the concave portion. Then, the method can include (i) a step of inserting the filter portion in the contracted state into the living body lumen, (ii) a step of installing the filter portion in the living body lumen by bringing the filter portion into the expanded state, (iii) a step of collecting the substances inside the living body lumen by using the filter portion, (iv) a step of inserting an aspiration catheter which can apply aspiration force to a distal opening via a lumen formed inside the aspiration catheter, into the living body lumen along the shaft portion, and fitting the distal opening into the concave portion of the filter portion, (v) a step of aspirating the substances collected inside the concave portion by using the aspiration catheter, (vi) a step of bringing the filter portion into the contracted state, and (vii) a step of removing the filter portion from the inside of the living body lumen. According to the method, the aspiration catheter can be caused to reach the inside of the concave portion by the shaft reaching the inside of the concave portion of the filter portion serving as a guide. Therefore, substances (debris) collected in the concave portion can be effectively aspirated and removed from the filter portion.

In addition, the above-described method may further include a step of scraping off stenosis substances or occluding substances formed inside the living body lumen on an upstream side (proximal side) of the filter portion, after the step of installing the filter portion in the living body lumen, and before the step of collecting the substances inside the living body lumen by using the filter portion. In this manner, the debris generated by the stenosis substances or the occluding substances being scraped off is filtered and collected by the filter portion. Accordingly, the debris can be effectively aspirated and removed from the filter portion by using the aspiration catheter.

In addition, according to the above-described method, in the step of bringing the filter portion into the contracted state, the filter portion may be brought into the contracted state by accommodating the filter portion inside the aspiration catheter. In this manner, the filter portion can be brought into the contracted state by using the aspiration catheter, thereby improving workability. In addition, the filter portion can be accommodated inside the aspiration catheter by applying aspiration force. In this manner, the filter portion can be contracted while the debris inside the filter portion is prevented from dropping down therefrom.

The present invention is not limited to the above-described embodiment, and can be modified in various ways within the technical idea of the present invention by those skilled in the art. For example, in the present embodiment, in the filter portion 50, the proximal side in an expanded state is concave to become the concave portion 53. However, depending on use, the distal side may be the concave portion.

In addition, the living body lumen into which the medical device 10 is inserted is not limited to the blood vessel. For example, the living body lumen may be vascular, ureteral, biliary, a fallopian tube, a hepatic duct, or the like. In addition, the medical device can be applied to another purpose in addition to the manipulation skill using the atherectomy device.

Figure 14:
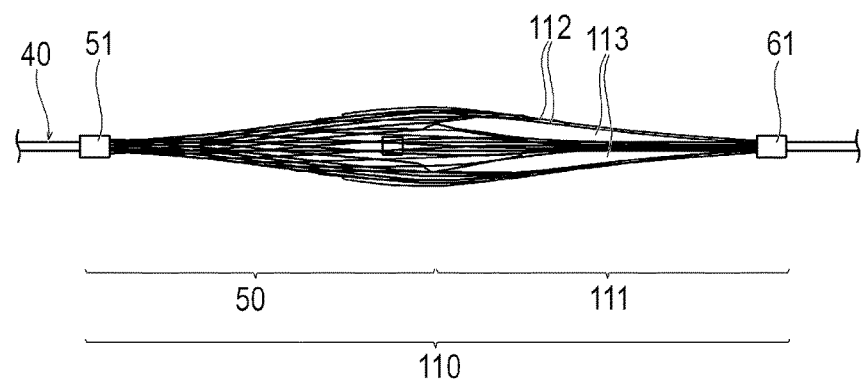
FIG. 14 is a plan view illustrating a modification example of the medical device according to the embodiment.

In addition, as in a modification example illustrated in FIG. 14, a support portion 111 of a deformation portion 110 may have a large gap 113 in such a way that wires 112 are twisted and collected to have a total number which is fewer than the number of wires 112. The same reference numerals are given to elements having the same function as the above-described embodiment, and description thereof will be omitted.

Figure 15:
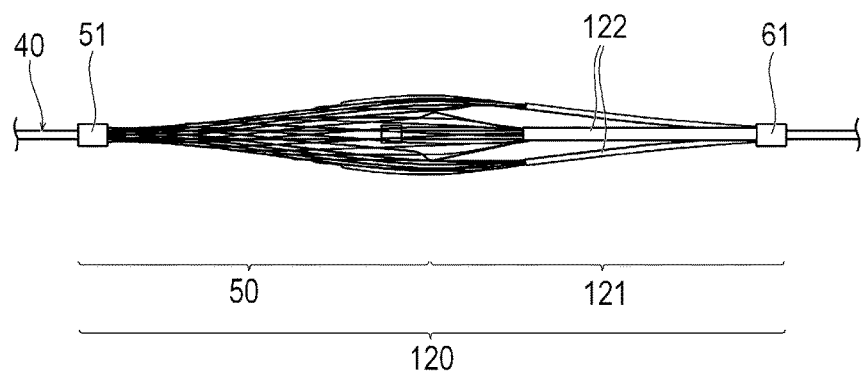
FIG. 15 is a plan view illustrating a modification example of the medical device according to the embodiment.

In addition, as in another modification example illustrated in FIG. 15, a support portion 121 of a deformation portion 120 may be configured to include a beam-shaped member 122 which is different from the wire configuring the filter portion 50.

Figure 16:
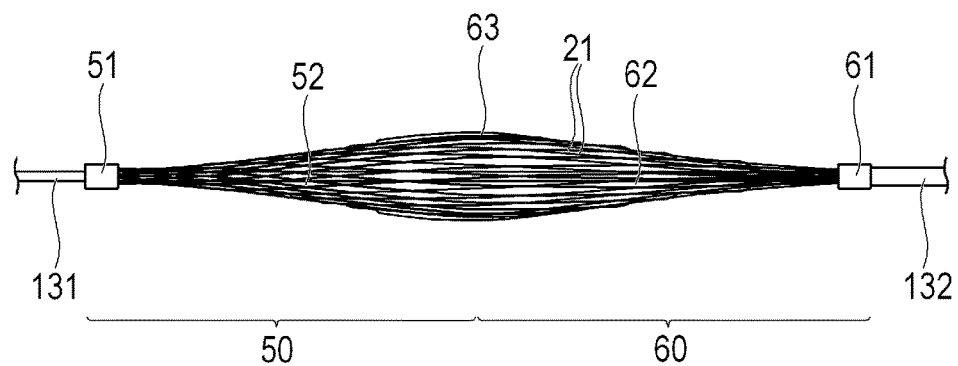
FIG. 16 is a plan view illustrating a modification example of the medical device according to the embodiment.

In addition, according to the above-described embodiment, in a natural state where external force is not applied, the filter portion 50 and the support portion 60 are brought into an expanded state. However, without being limited thereto, the filter portion 50 and the support portion 60 may be brought into a contracted state in a natural state. In this case, the external force is applied so as to deform the filter portion and the support portion, thereby bringing the filter portion and the support portion into the expanded state. For example, as in still another modification example illustrated in FIG. 16, a shaft portion 131 is interlocked with the filter side connection portion 51 of the filter portion 50, and an outer tube 132 for covering the shaft portion 131 is interlocked with the support side connection portion 61 of the support portion 60. Then, the shaft portion 131 and the outer tube 132 are relatively moved, and the filter side connection portion 51 and the support side connection portion 61 are moved close to each other. In this manner, the filter portion 50 and the support portion 60 can be deformed to be in an expanded state.

Figure 17:
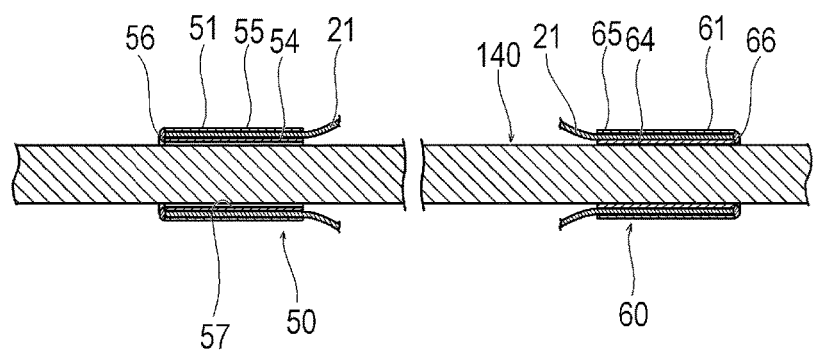
FIG. 17 is a cross-sectional view illustrating a modification example of the medical device according to the embodiment.
Figure 18:
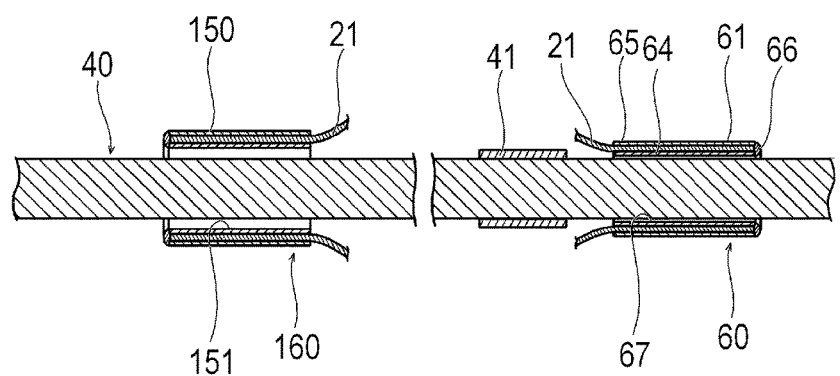
FIG. 18 is a cross-sectional view illustrating a modification example of the medical device according to the embodiment.

In addition, as illustrated in FIG. 17, a shaft portion 140 may be fixedly attached to the support side connection portion 61. In addition, as illustrated in FIG. 18, a configuration may be adopted in which the stopper portion 41 of the shaft portion 40 can pass through a through-hole 151 of a filter side connection portion 150. According to this configuration, in an expanded state, the shaft portion 40 is moved relatively to the proximal side from the sheath 30, thereby causing the stopper portion 41 to press the support side connection portion 61 toward the proximal side. In this manner, the support portion 60 and a filter portion 160 can also be drawn into the lumen 34 of the tubular body 31. In addition, according to this configuration, after only the shaft portion 40 from which the filter portion 160 is detached is inserted to reach a desired position, the proximal end portion of the shaft portion 40 is inserted into the filter side connection portion 150, and the stopper portion 41 is caused to pass through the through-hole 151 of the filter side connection portion 150 by moving the filter portion 160 to the distal side of the shaft portion 40. In this manner, the filter portion 160 can be located in the vicinity of the distal end portion of the shaft portion 140.

In addition, at least a portion of the filter portion 50 including the filter side connection portion 51 and the wires 21, the support portion 60 including the support side connection portion 61 and the wires 21, and the shaft portion 40 including the stopper portion 41 may be formed so that a configuration material of the filter portion 50, the support portion 60, and the shaft portion can contain a material having X-ray contrast performance. For example, a portion of the multiple wires 21 may be formed so that the configuration material contains the material having X-ray contrast performance. In this manner, a position can be accurately recognized by using X-ray contrast. Accordingly, required manipulation skill becomes easier. For example, as the material having X-ray contrast performance, it can be preferable to use gold, platinum, a platinum-iridium alloy, silver, stainless steel, molybdenum, tungsten, tantalum, palladium, or an alloy thereof.

The detailed description above describes a collection method. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A collecting method for collecting substances from a stenosis site or an occluded sited formed inside a living body lumen using a medical device including an elongated shaft portion, a filter portion that has multiple gaps, that is formed in a net shape, and that is deformable to be in an expanded state where the filter portion has a basket shape so as to form a concave portion and is deformable from the expanded state to be in a contracted state where an opening end portion of the concave portion is contracted, and a support portion that is formed to include a gap larger than the gaps of the filter portion, and that includes an interlock portion interlocked with the opening end portion of the filter portion and a support side connection portion connected to the shaft portion, in which in the expanded state, the support side connection portion can be located inside the concave portion of the filter portion, and in the contracted state, the interlock portion contracts with the opening end portion, and the support side connection portion is located away from the filter portion so as to protrude outward from the concave portion, the method comprising:

inserting an introduction sheath into the living body lumen on an upstream side from the stenosis site or the occluded site;
 inserting a guidewire into the living body lumen via the introducer sheath;
 pushing the guidewire forward so as to reach a proximal side of the stenosis site or the occluded site;
 inserting the proximal end portion of the guide wire located extracorporeally into a catheter opening on a distal side of a guiding catheter;
 inserting the guiding catheter into the living body lumen along the guidewire so as to reach the proximal side of the stenosis site or the occluded site;
 inserting the proximal end portion of the guidewire located extracorporeally into a catheter opening on a distal side of a support catheter;
 pushing the support catheter forward to reach the proximal side of the stenosis site or the occluded site;
 removing the guidewire in a state where the support catheter remains inside the living body lumen;
 inserting the medical device into the living body lumen via the support catheter so as to reach the distal side of the stenosis site or the occluded site;
 removing the support catheter;
 inserting the filter portion in the contracted state into the living body lumen;
 installing the filter portion in the living body lumen by bringing the filter portion into the expanded state;
 collecting the substances inside the living body lumen using the filter portion;
 inserting an aspiration catheter which applies an aspiration force to a distal opening via a lumen formed inside the aspiration catheter, into the living body lumen along the shaft portion, and fitting the distal opening into the concave portion of the filter portion;
 aspirating the substances collected inside the concave portion using the aspiration catheter;
 bringing the filter portion into the contracted state; and
 removing the filter portion from the inside of the living body lumen.

2. The collecting method according to claim 1, comprising:
 scraping off substances at the stenosis site or the occluded site on an upstream side of the filter portion, after the installing the filter portion in the living body lumen, and before the collecting the substances inside the living body lumen using the filter portion.

3. The collecting method according to claim 1, wherein the bringing the filter portion into the contracted state comprises:
 bringing the filter portion into the contracted state by accommodating the filter portion inside the aspiration catheter.

4. The collecting method according to claim 1, wherein in a state where an external force is not applied, the filter portion and the support portion are shaped so as to be in the expanded state.

5. The collecting method according to claim 1, comprising:
 a through-hole formed in the support side connection portion; and
 connecting the shaft portion to the through-hole by slidably penetrating the through-hole in the support side connection portion.

6. The collecting method according to claim 5, comprising:
 a through-hole formed in a filter side connection portion; and
 connecting the shaft portion to the through-hole by slidably penetrating the through-hole in the filter side connection portion on a side opposite to the interlock portion of the filter in the contracted state, and
 wherein the shaft portion has a stopper portion which is located between the support side connection portion and the filter side connection portion, and wherein the stopper portion has a size which cannot pass through the support side connection portion and the filter side connection portion.

7. The collecting method according to claim 1, comprising:
 a tubular sheath that accommodates the filter portion and the support portion in the contracted state, and prevents the filter portion and the support portion from being deformed in the expanded state.

8. The collecting method according to claim 1,
 providing at least a portion of the filter portion, the support portion, and the shaft portion with an X-ray contrast property.

9. The collecting method according to claim 1, wherein the medical device includes a tubular sheath; and
 moving the tubular sheath to the proximal side from the filter portion, and causing the filter portion to protrude to the distal side from the elongated shaft portion such that a deformation portion is brought into the expanded state by material properties of the filter and wherein an outer peripheral portion of the filter portion, which has the basket shape comes into contact with an inner wall surface of the living body lumen.

10. The method according to claim 9, wherein the material properties of the filter comprises the filter being made from a shape memory alloy.

* * * * *